United States Patent
Laboureau et al.

(10) Patent No.: US 6,866,681 B2
(45) Date of Patent: *Mar. 15, 2005

(54) PRE-ADJUSTED PROSTHETIC LIGAMENT AND METHOD OF MANUFACTURE

(75) Inventors: Jacques-Phillippe Laboureau, 24, rue Fontaine Billenois, F-21000, Dijon (FR); Bernard Brulez, Bourbonne les Bains (FR)

(73) Assignee: Jacques-Phillippe Laboureau, Dijon (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 567 days.

(21) Appl. No.: 09/308,548
(22) PCT Filed: Nov. 19, 1997
(86) PCT No.: PCT/FR97/02082
§ 371 (c)(1),
(2), (4) Date: May 20, 1999
(87) PCT Pub. No.: WO98/22046
PCT Pub. Date: May 28, 1998

(65) Prior Publication Data
US 2001/0044659 A1 Nov. 22, 2001

(30) Foreign Application Priority Data
Nov. 20, 1996 (FR) .......................................... 96 14263

(51) Int. Cl.⁷ ................................................. A61F 2/08
(52) U.S. Cl. ....................... 623/13.2; 623/901; 623/909
(58) Field of Search ........................... 623/13.11, 13.19, 623/13.2, 13.12, 13.13, 13.14, 901, 909; 87/7, 8, 9, 11

(56) References Cited

U.S. PATENT DOCUMENTS

| 3,805,667 | A | * | 4/1974 | Orser ................................ 87/6 |
| 4,187,558 | A | * | 2/1980 | Dahlen et al. ............ 623/13.14 |
| 4,713,075 | A | * | 12/1987 | Kurland ....................... 128/898 |
| 4,792,336 | A | * | 12/1988 | Hlacek et al. ............ 623/13.18 |
| 4,917,699 | A | * | 4/1990 | Chervitz ................... 623/13.19 |
| 5,078,744 | A | * | 1/1992 | Chvapil ........................ 606/86 |
| 5,176,708 | A | * | 1/1993 | Frey et al. ................. 623/13.2 |
| 5,263,984 | A | | 11/1993 | Li et al. |
| 5,425,766 | A | * | 6/1995 | Bowald ........................ 623/13 |

FOREIGN PATENT DOCUMENTS

| DE | 3923580 A | | 1/1991 |
| EP | 0561710 A1 | | 9/1993 |
| FR | 2651994 | | 3/1991 |
| FR | 459914 | * | 12/1991 |
| FR | 2697151 | | 4/1994 |

* cited by examiner

Primary Examiner—Brian E Pellegrino
(74) Attorney, Agent, or Firm—Greensfelder, Hemker & Gale, P.C.

(57) ABSTRACT

A prosthetic ligament and its method of manufacture is provided by which the prosthetic ligament is comprised of a plurality of strands aligned in a parallel lengthwise relationship to form a bundle, with the strands being interwoven at their respective ends while the middle portion of the strands remain unattached to adjacent strands. A predetermined torsion is applied to each strand prior to forming the bundle to create natural coiling in either a clockwise or counterclockwise orientation. The prosthetic ligament may be used for a posterior or anterior cruciate ligament of the knee joint.

9 Claims, 3 Drawing Sheets

PRE-ADJUSTED PROSTHETIC LIGAMENT AND METHOD OF MANUFACTURE

Figure 1:
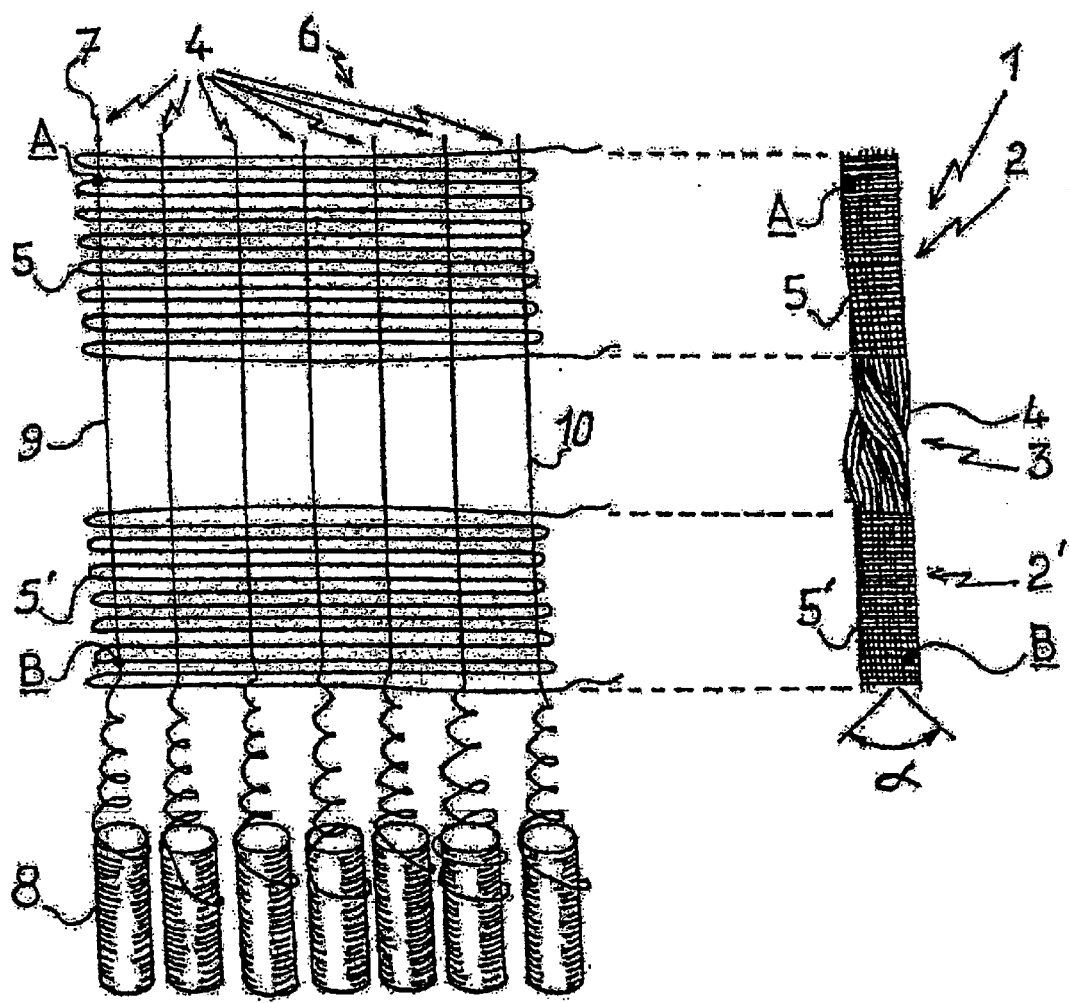

The invention relates to a left or right-oriented prosthetic ligament to replace a biological joint ligament, and to several methods for making such pre-oriented ligaments; these left-gyratory or right-gyratory ligaments can be especially used in knee plasty to replace anterior or posterior cruciate ligaments whether for left or right knee joints.

A certain number of artificial ligaments intended to replace joint ligaments are already known to the prior art. Such ligaments include those obtained by convoluted folding or rolling of fabric strips in biocompatible material, whether woven or knitted such as to leave free, or on the contrary join together, the technical longitudinal strands of the ligament.

This is particularly the case for the ligaments described in French patent FR-2 697 151 filed by the applicant which, in addition to the high dynamometric properties of previous prostheses, provide for further improved response of ligaments to the demands placed upon them after implant, through their close approximation of the geometry and configuration of the anatomic ligaments. For this purpose, an artificial ligament was provided, comprising two intra-osseous ends, and an intra-articular intermediate part, characterised in that the intra-articular part was formed of two independent cords of longitudinal fibres obtained by convoluted rolling of at least one knitted width of fabric, partly slit at its median portion over a distance at least equal to that of the intra-articular part, both intra-osseous ends being twisted by at least one quarter of a turn in relation to one another when the ligament is in place within the joint.

It is known that this type of ligament offers qualities that are related to the twin-cord structure which, in particular for the replacement of the anterior cruciate ligament of the knee, provides an undeniable biomechanical advantage since it has been well proven that the anterior cruciate ligament undergoes more than 45° torsion when the knee moves from maximum flexion to maximum extension; therefore, by implanting an artificial ligament that is pre-oriented in the same direction as this natural torsion movement between the tibia and the internal femoral condyle, on a flexed knee, it is possible to cause the two cords forming the ligament to untwist when the knee is in extension, and they then display a perfectly parallel structure.

With this possibility, the longitudinal strands which make up the technical core of the ligament become parallel to one another when the knee is close to extension, that is to say in the position in which it usually suffers trauma when sprained; when stresses are applied, demand is placed upon these strands in progressive manner forming a true shock-absorbing system that reproduces the anatomical process.

Nonetheless, it is known that this effect can only be truly substantial with an artificial ligament if there are a sufficient number of longitudinal strands which can be activated on demand to surround the isometric neutral fibre as closely as possible, which implies a prosthetic construction comprising the greatest number of strands in the smallest cylindrical volume; it is recalled in passing that the neutral fibre of a ligament is the one which passes through the isometric axis joining together the isometric points of the bones of the joint involved.

It is easy to understand that in a twin-bundle configuration such as provided by the prior art, it is difficult to achieve instant response from a sufficient number of longitudinal strands around the neutral fibre.

It therefore appeared that an artificial ligament such as described in French patent FR 2 688 690 by the same applicant, characterised in that its intra-articular part is solely made up of adjacent strands that are not connected together, could advantageously achieve this effect; according to the teachings given by this prior document, the ligament used is made from a width of fabric which preserves the parallelism of the adjacent strands which can consequently resist the efforts applied to the implanted ligaments, in line with their own longitudinal direction.

On account of its intra-articular structure that is non-woven, non-knitted and more generally has no weft, it is possible to considerably increase the number of active strands while maintaining the same volume capacity as a ligament that is knitted or woven over its entire length; in this way it is virtually possible to double the number of active strands of the ligament.

Also, this more compact structure of the active strands brings the latter closer to the "neutral fibre" of the ligament.

The drawback of this type of so-called "free-strand" ligament is that it cannot be naturally coiled around itself in its intra-articular median portion, as can the twin-bundle ligament described in French patent FR 2 697 151 already described.

The purpose of the present invention is precisely to provide a "free strand" ligament that is naturally self-convoluted between the two ends of the intra-articular median part.

In this respect, the invention provides a method of producing a prosthetic ligament for the replacement of a natural joint ligament, comprising between two end parts a median part that is solely made up of a bundle of so-called "active" strands in mono or multi-filament of 1200 decitex or less, that are longitudinal, adjacent and not bound to one another in crosswise direction, characterised in that prior to the assembly of the ligament a longitudinal torsion is imparted to each active strand, a clockwise or anti-clockwise direction of torsion being chosen so as to form respectively a prosthetic ligament for right joint or left joint, the ends of the active strands being held together by any appropriate means over a sufficient distance to form the end parts of the prosthetic ligament intended to be embedded into the bone tunnels of the joint.

All the advantages of this method are easy to understand since the manner described below, in which sufficient torsion is imparted to each active strand, is all that is required for the resulting torque to create natural coiling of the ligament by at least one eighth of a turn between the two ends of the active median portion, corresponding in practice to optimal torsion at least when the bony insertion tunnels are ideally situated.

Bearing in mind also that in a knee flexed at 90°, the two bundles of the biological anterior cruciate ligament are coiled in clockwise direction for the right knee and in anti-clockwise direction for the left knee, and in accordance with an essential characteristic of the invention, the direction of torsion of the active strands of the prosthesis is advantageously chosen between a clockwise or anticlockwise direction, determining respectively a prosthetic ligament for a right or left joint.

Figures 2A, 2B:
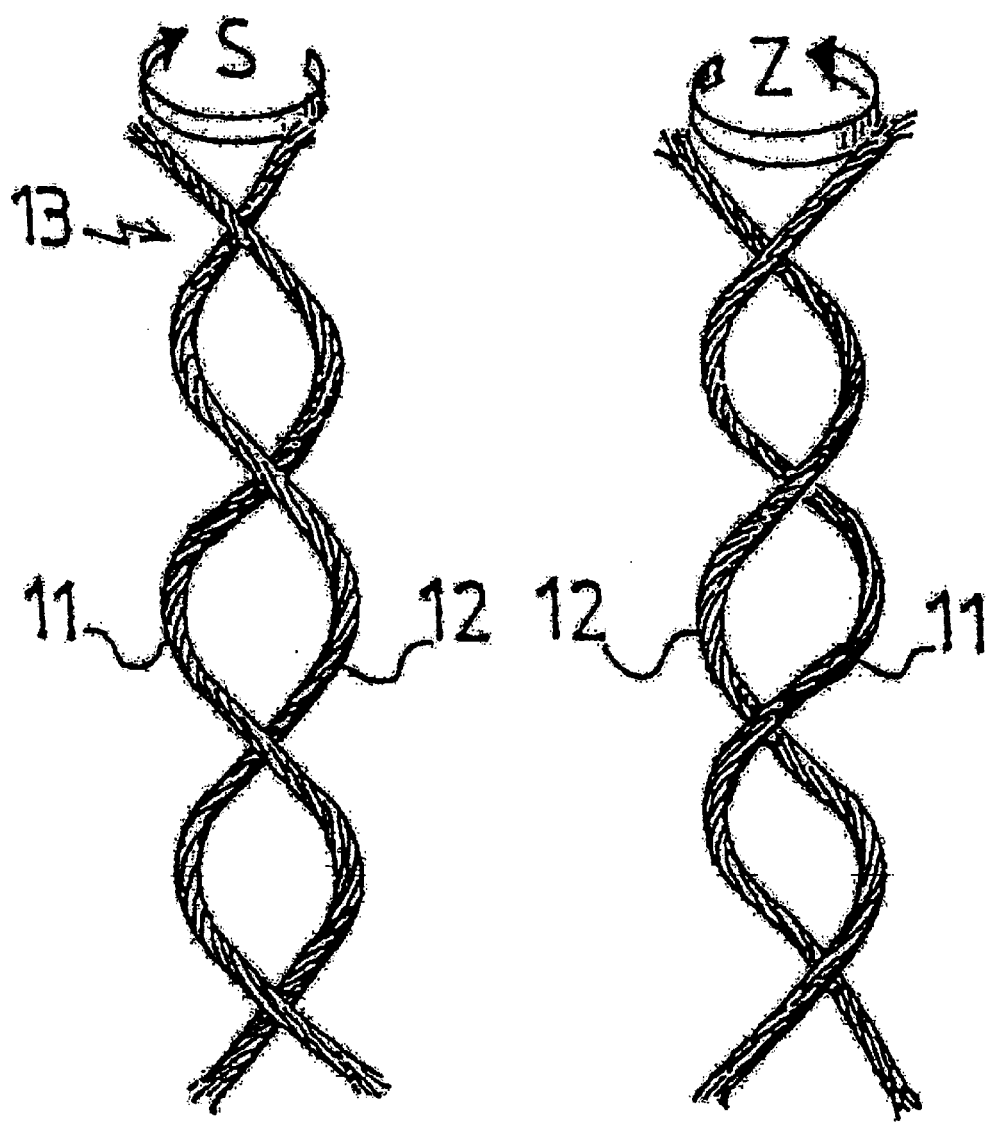

Other characteristics and advantages will be better understood from the following description of several methods of imparting torsion to the active strands according to whether a bundle of mono-filament or multi-filament strands is used, at least in the intra-articular portion of the prosthetic ligament, this description being given for illustrative purposes and is non-restrictive with reference to the drawings in which:

FIG. 1 is a diagram of the main stages of a first variant of the torsion method for the active strands in a continuous, parallel mono-filament or multi-filament configuration, FIG. 2 shows two diagrams of cable twisted threads able to impart natural torsion to each assembly either in clockwise direction (diagram S) (FIG. 2a) or anti-clockwise direction (diagram Z) (FIG. 2b), FIG. 3 is an elevation view of the prosthetic ligaments: left-gyratory (3a) right-gyratory (3b) and left-gyratory with two convoluted rolls (3c).

With reference to FIG. 1 a first variant of the method of producing prosthetic ligament 1 will be described intended to replace a natural joint ligament such as for example the anterior or posterior cruciate ligaments of the knee. Said prosthetic ligament 1 comprises two end parts 2, 2' normally intended to be embedded in the bone insertion tunnels of the joint; around end parts 2, 2', a median portion 3 is exclusively made up of a bundle of active strands 4; active strands 4, advantageously in a biocompatible polyester type material, may be either mono-filament or multi-filament, that is to say made up of a certain number of continuous filaments placed parallel to one another to form a single thread 4 which must be as thin as possible while remaining sufficient to resist the stresses to which each type of ligament is subjected; taking into consideration the tests conducted, the best results are obtained with polyester filaments having a maximum decitex value of 1200, such as for example the filaments carrying the reference PES TYPE 156 made by Rhône Poulenc.

For all that follows, median part 4 of ligament 1 corresponds most precisely to the intra-articular portion of the joint to be repaired, for example the knee.

Active strands 4 forming median part 3 of ligament 1 are held at their upper and lower ends by an assembly of weft threads 5, 5' connecting them crosswise; thread assemblies 4, 5, 5' make up the end parts 2 and 2' of the intra-osseous part of ligament 1.

This type of assembly is known from French patent FR 2 688 690 already described in the preamble.

According to one variant of the method of the invention, ligament 1 is made such that it naturally has an active median portion twisted around itself at an angle a that is ideally 45° or greater, such as shown in the diagram in FIG. 1 by references A and B vertically aligned on the left side of FIG. 1 showing the step-by-step assembly of fabric width 6 such as described below, and staggered at an angle a on the right side showing a finished ligament.

Taking into account that active strands 4 are unattached crosswise in median part 3 of the ligament, the latter cannot have a natural torque A, B. Under these conditions, the invention provides that, at the time of preparation of fabric width 6, a longitudinal torsion in the same direction and of the same value is imparted to each active strand 4. To confer this torsion upon each active strand 4, said strands 4 are unwound axially starting from their free end 7 from fixed spools 8 whose original direction of winding will determine the final direction of torsion of each strand 4.

It can be understood that since spools 8 dispensing strands 4 are fixed, and since end 7 of each strand 4 is pulled vertically and held without compensation, the latter will coil around itself in a spiral whose pitch is equivalent to one turn of the spool, the diameter of the latter determining the torsion angle per unit length.

It is hence understood that it is easy to adjust the torque of each strand 4 by choosing the direction of winding of the strand on each spool 8 whose diameter determines final torque value.

All strands 4 thus coiled being positioned parallel to one another and forming the warp of fabric width 6, all that is needed is a well-known manner to produce an assembly of strands 4 with the use of cross threads 5, 5' advantageously of the same quality, to form the weft of fabric width 6 at least on two side strips corresponding to the bone end parts 2, 2' of the ligament such as shown on the left of FIG. 1; it raises no problem to produce a fabric width 6 using any technique known to persons skilled in the art, for example, by weaving, knitting, braiding, stitching or similar etc . . . such that the same fabric width 6 when rolled over itself from one of its edges 9 or 10 provides a ligament 1 with free strands 4 corresponding to the central space of fabric width 6 lying between the two picked side strips.

Figure 3A:
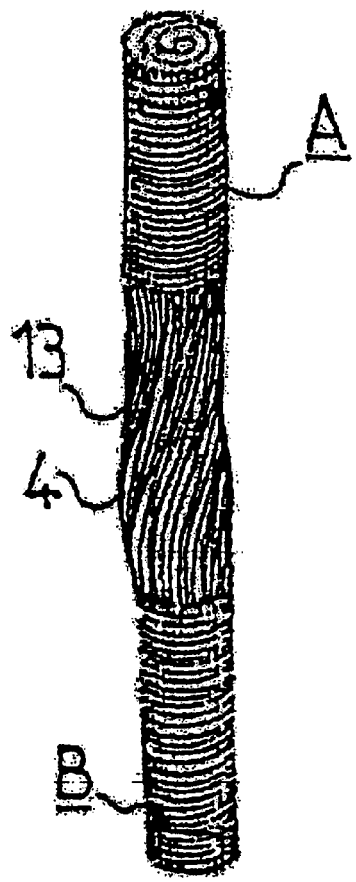
Figure 3B:
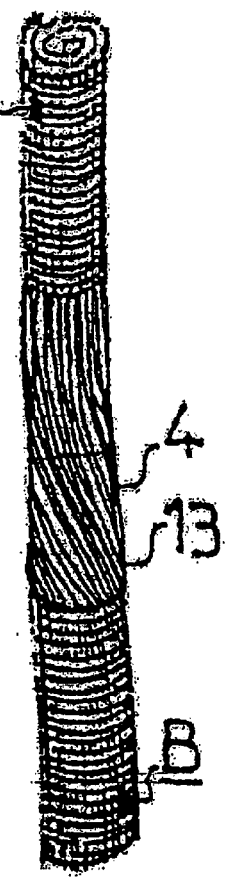
Figure 3C:
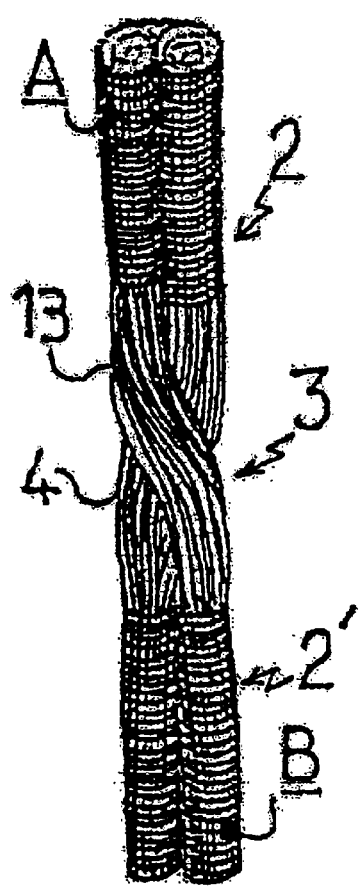

Evidently, several variants remain possible for making a ligament by convoluted rolling of fabric width 6; for example a single-bundle ligament 1 can be obtained by simply rolling either from edge 9 or from edge 10 of fabric width 6 in concentric turns, the last turn being stitched longitudinally to the preceding turn on these two end parts 2 and 2', as shown in FIG. 3a and 3b; ligament 1 can also be made by convoluted rolling inwards from each opposite edge 9, 10, the two bundles when they meet being stitched longitudinally on the two end parts 2 and 2' producing a ligament with two longitudinal axes that is closer to the anatomy as shown in the diagram in FIG. 3c.

Irrespective of how fabric width 6 is rolled, it is evident that the inner torsion imparted to each active strand 4 will, on median part 3 of ligament 1, give rise to a torque having the same value and same direction on all the free strands, such that the ligament will naturally coil around itself. Evidently it is possible, by reversing the direction of winding of spools 8 at the time of manufacture of fabric width 6, to produce ligaments 1 whose natural torsion is oriented right (FIGS. 3a and 3c) or left (FIG. 3b).

This essential characteristic of the ligaments of the invention will, as has been seen, enable virtually ideal replacement of a torn biological ligament by a prosthesis that is anatomically very similar. It has already been mentioned for example that the anterior cruciate ligament undergoes approximately one eighth of a turn torsion when the knee moves from maximum flexion to maximum extension. However prosthetic anterior cruciate ligaments are generally implanted with the knee in maximum flexion. It is therefore fully advantageous to implant a ligament that is pre-coiled according to the method detailed above, which will provide biomechanical stability and isometric properties that are almost ideal. Also, this type of ligament whose active median part 3 is made up of longitudinal strands 4 unconnected to one another in crosswise direction and pre-oriented as per right or left intrinsic coiling, is the only one which can not only prevent the torque stresses usually suffered by ligaments which are the main cause of their rupture, but also reproduces the phenomenon of gradual demand on fibres when the ligament is suddenly placed under stress. Mechanical laboratory tests, conducted on machines reproducing knee kinetics, have shown that the ligaments such as described in the present invention have a much higher resistance to fatigue than the ligaments of the prior art, including those described by the applicant in patents FR-2 697 151 and FR-2 688 690.

According to another variant of the method of the invention, to obtain a right or left torsion of the active strands, it may be advantageous to cable twist two strands 11, 12 (which may each be made up of one or several filaments as mentioned above), that are torsion mounted, that is to say coiled around themselves in either direction in accordance with the diagram given in FIG. 2 which shows a clockwise torsion S and an anti-clockwise torsion Z. It is easy to understand that each cable cord has natural torsion in a given direction; in this case, all that is required is to replace active strands 4 of the previous method by a cable cord 13 to obtain a fabric width 6 in the same manner which, when rolled over from one of its edges or from both edges, will form a ligament in accordance with either one of the diagrams in FIG. 3.

Here too the intra-osseous end parts 2 and 2' of prosthetic ligament 1 correspond, as seen above, to the knitted woven, braided, stitched or similar part of fabric width 6 using weft threads 5, 5'; also median part 3 of ligament 1, obtained with cable cords 13 that are free in crosswise direction and parallel to one another, will correspond precisely to the intra-articular portion of the prosthesis when implanted in the joint.

In this respect, it is remarkable to observe that it is possible using the methods of the invention, to obtain ligaments that are fully adapted to the ligament plasty under consideration; it can, for example, be planned that the length of median portion 3 of ligament prosthesis 1, whether made with a bundle of strands 4 or cable cords 13, should be 30 mm to act as a prosthetic anterior cruciate ligament, or 45 mm to act as a posterior cruciate ligament.

Needless to say, for each type of ligament prosthesis, the choice of ligament corresponding to a right or left joint must also be made, resulting, as mentioned above, from the clockwise or anti-clockwise torsion of active strands 4 or cable cords 13.

Evidently any other method intended to impart torsion either to cable cords 13 or active strands 4 would come under the scope of the method for producing pre-oriented prosthetic ligaments in accordance with the main characteristic of the invention.

What is claimed is:

1. A method for producing a prosthetic ligament to replace a natural joint ligament, said method comprising:
    first applying a predetermined torsion individually to each of a plurality of strands,
    thereafter forming a bundle of said strands aligned in a parallel lengthwise relationship, each strand having a median part and first and second end parts,
    securing said strands to each other at said respective first and second end parts to form first and second end sections of said bundle, said first and second end sections forming respective end members of said prosthetic ligament, and having sufficient length to be embedded in bone insertion tunnels of a joint, and
    leaving said median parts of said strands unattached to collectively form a middle section of said bundle, said middle section of said bundle comprising a central member of said prosthetic ligament approximating a length of an intra-articular portion of a natural ligament.

2. The method for producing a prosthetic ligament according to claim 1 in which said torsion is applied to said strands to a sufficient degree to create natural coiling of said prosthetic ligament by at least one eighth of a turn between said end members.

3. The method for producing a prosthetic ligament according to claim 1 which said torsion is applied to said strands by unwinding each of said strands from a fixed spool, each said strand being pulled in an axial direction relative to said spool, and perpendicular to a concentric winding direction of said strand around said spool.

4. The method for producing a prosthetic ligament according to claim 1 in which said applied torsion has a same direction and value for each strand.

5. The method for producing a prosthetic ligament according to claim 1 in which said bundle in a pre-formed stage comprises a flat fabric of laterally arrayed strands connected together side by side at their respective end parts, said fabric having exterior longitudinal edges formed from respective outermost strands, said fabric being adapted to be rolled longitudinally in concentric turns beginning at a first exterior longitudinal edge and terminating at a second longitudinal edge to form said bundle, said second longitudinal edge being secured against said fabric to prevent said bundle from unrolling.

6. The method for producing a prosthetic ligament according to claim 1 in which said bundle in a pre-formed stage comprises a flat fabric of laterally arrayed strands connected together side by side at their respective end parts, said fabric having exterior longitudinal edges formed from respective outermost strands, said fabric being adapted to be rolled longitudinally inwards upon itself in concentric turns beginning at each of said outermost strands such that two symmetrical bundles are formed.

7. The method for producing a prosthetic ligament according to claim 1 in which each of said strands comprises at least a pair of fibers wrapped around each other to form a twisted cable.

8. The method for producing a prosthetic ligament according to claim 7 in which a direction of twisting of said twisted cable is made in a clockwise orientation to create a natural torsion of said prosthetic ligament for adaptation with a right joint.

9. The method for producing a prosthetic ligament according to claim 7 in which a direction of twisting of said twisted cable is made in a counter-clockwise orientation to create a natural torsion of said prosthetic ligament for adaptation with a left joint.

* * * * *